(12) United States Patent
Mechery et al.

(10) Patent No.: US 7,239,766 B2
(45) Date of Patent: Jul. 3, 2007

(54) OPTICAL SENSING ELEMENTS FOR NITROGEN DIOXIDE ($NO_2$) GAS DETECTION, A SOL-GEL METHOD FOR MAKING THE SENSING ELEMENTS AND FIBER OPTIC SENSORS INCORPORATING NITROGEN DIOXIDE GAS OPTICAL SENSING ELEMENTS

(75) Inventors: Shelly John Mechery, Mississippi State, MS (US); Jagdish P. Singh, Starkville, MS (US)

(73) Assignee: Mississippi State University, Mississippi State, MS (US)

( * ) Notice: Subject to any disclaimer, the term of this patent is extended or adjusted under 35 U.S.C. 154(b) by 129 days.

(21) Appl. No.: 10/693,519

(22) Filed: Oct. 27, 2003

(65) Prior Publication Data

US 2005/0089260 A1 Apr. 28, 2005

(51) Int. Cl.
*G02B 6/00* (2006.01)
(52) U.S. Cl. .................................... 385/12; 436/116
(58) Field of Classification Search ............... None
See application file for complete search history.

(56) References Cited

U.S. PATENT DOCUMENTS

| | | | | |
|---|---|---|---|---|
| 3,718,543 | A * | 2/1973 | Lagomarsino | 435/37 |
| 4,925,268 | A * | 5/1990 | Iyer et al. | 385/12 |
| 5,567,622 | A | 10/1996 | Jadiszliwer et al. | 436/106 |
| 5,582,170 | A * | 12/1996 | Soller | 600/322 |
| 6,207,098 | B1 * | 3/2001 | Nakanishi et al. | 264/414 |
| 6,362,005 | B1 | 3/2002 | Tanaka et al. | 436/117 |
| 6,445,861 | B1 * | 9/2002 | Shaw et al. | 385/123 |
| 2003/0068827 | A1 * | 4/2003 | Morris et al. | 436/136 |

OTHER PUBLICATIONS

O. Worsfold et al. Optical NO2 sensing based on sol-gel entrapped azobenzene dyes. Sensors and Actuators B, 56, pp. 15-21, Jul. 1999.*

M. John et al. Self-calibrated fiber optic transflection probe for NO2 detection. Industrial and Highway Sensors Technology, Proc. SPIE 5272, pp. 110-115, Mar. 2004.*

T. Tanaka et al. Coloration reactions between NO2 and organic compounds in porous glass for cumulative gas sensor. Sensors and Actuators B, 47, pp. 65-69, Apr. 1998.*

(Continued)

*Primary Examiner*—Rodney Bovernick
*Assistant Examiner*—Mike Stahl
(74) *Attorney, Agent, or Firm*—DLA Piper US LLP

(57) ABSTRACT

A sensing element, a method of making a sensing element, and a fiber optic sensor incorporating the sensing element are described. The sensor can be used for the quantitative detection of $NO_2$ in a mixture of gases. The sensing element can be made by incorporating a diazotizing reagent which reacts with nitrous ions to produce a diazo compound and a coupling reagent which couples with the diazo compound to produce an azo dye into a sol and allowing the sol to form an optically transparent gel. The sensing element changes color in the presence of $NO_2$ gas. The temporal response of the absorption spectrum at various $NO_2$ concentrations has also been recorded and analyzed. Sensors having different design configurations are described. The sensing element can detect $NO_2$ gas at levels of parts per billion.

21 Claims, 11 Drawing Sheets

OTHER PUBLICATIONS

Saltzman, "Colorimetric Microdetermination of Nitrogen Dioxide in the Atmosphere", Anal. Chem. 26, 1949-1955 (1954).

Harper et al., "Detection of Nitric Oxide and Nitrogen Dioxide with Photoluminescent Porous Silicon", Anal. Chem. 68, 3713-3717 (1996).

K.T.V. Grattan and T. Sun, "Optical Fiber Sensor Technology: Fundamentals", Kluwer Academic Publishers, Dordrecht (1999).

Krohn, "Fiber Optic Sensor: Fundamentals and Applications", ISA-Instrumentation, Systems, and Automation Society, North Carolina (2000).

B. Culshaw and J.P. Dakin, "Optical Fiber Sensing and Signal Processing", Peter Peregrinus Ltd., London (986) and "Optical Fiber Sensors: Components and Subsystems", Artech House, Inc., London (1996).

* cited by examiner

OPTICAL SENSING ELEMENTS FOR NITROGEN DIOXIDE (NO₂) GAS DETECTION, A SOL-GEL METHOD FOR MAKING THE SENSING ELEMENTS AND FIBER OPTIC SENSORS INCORPORATING NITROGEN DIOXIDE GAS OPTICAL SENSING ELEMENTS

This U.S. Government has certain rights in this invention as provided for by the terms of Contract No. DE-FC26-98FT-40395, awarded by the United States Department of Energy.

BACKGROUND

1. Technical Field

The present application relates generally to the detection of pollutants in air. In particular, the present application relates to a fiber optic gas sensor which can detect $NO_2$ in a mixture of gases. The sensor is capable of quantitatively measuring nitrogen dioxide gas uniformly blended in air at concentrations as low as a few parts per billion.

2. Background of the Technology

Nitrogen oxides ($NO_x$) are recognized as one of the primary air pollutants. The continued or frequent exposure may cause respiratory illness or harm the lung functions in human beings. Apart from the health hazards, $NO_x$ are important precursor to both ozone and acid rain. A major part of this pollutant gas is released from localized sources, primarily from the combustion factories and automobile exhausts. The continuous monitoring as well as quantitative detection of these gases at trace amount is always essential. A mechanism that provides accurate information about the pollutant level in the environment and enables to take the adequate steps to keep the normal environmental standards is highly needed.

Conventionally the measurement of $NO_2$ concentrations has been carried out using analytical instruments based on the Saltzman method and chemiluminescence technique, as explained in Saltzman, "Colorimetric Microdetermination of Nitrogen Dioxide in the Atmosphere", Anal. Chem. 26, 1949-1955 (1954); and Harper et al., "Detection of Nitric Oxide and Nitrogen Dioxide with Photoluminescent Porous Silcon", Anal. Chem. 68, 3713-3717 (1996). Recently efforts to develop devices to quantitatively detect these highly toxic pollutants have come forward. The development of various devices based on semiconductor gas sensing, solid-electrolyte gas sensors, electrochemical gas sensors and quartz crystal gas monitors etc. are few examples in the gas sensing devices in this direction. These devices have certain drawbacks. For example, some of these devices require high operating temperatures. Others require a reference electrode or exhibit short lifetimes. In all these methods the sampling of the gas is a difficult procedure.

A common simple measurement method is to receive air using a pump, collect $NO_2$ gas by directly collecting it into a sampling bag (i.e., a direct collection method). An alternative method involves using a solid-state adsorbent (i.e., a solid collection method) or by collecting into an absorbing solution (i.e., a liquid collection method) and analyzing the collected gas by the gas chromatography. In all of these methods it is necessary to transport not only samples but also peripheral apparatuses such as a pump etc. In the direct collection method, it is difficult to store the gas because the size of the sampling bag is limited. The solid collection method and the liquid collection method require a process of sensing the collected gas. In comparison to these conventional $NO_2$ sensing schemes, fiber optic sensors (FOS) are particularly a promising alternative. For example, the sensor can be installed at different locations and eliminates many of the difficulties rendered by other sensing schemes.

Fiber optic sensors (FOS) have specific advantages such as geometrical versatility, small dimension, lightweight and remote sensing capabilities etc. Moreover these sensors offer complete electrical isolation and are totally isolated from the electromagnetic and radio frequency interferences. See, for example, Grattan and Meggitt. Eds., "Optical Fiber Sensor Technology: Fundamentals", Kluwer Academic Publishers, Dordrecht (1999) and Krohn, "Fiber Optic Sensors: Fundamentals and Applications", ISA-Instrumentation, Systems, and Automation Society, North Carolina (2000). Also a variety of applications of fiber optic sensors are disclosed in Culshaw, "Optical Fiber Sensing and Signal Processing", Peter Peregrinus Ltd., London (986) and "Optical Fiber Sensors: Components and Subsystems", Artech House, Inc., London (1996).

U.S. Pat. No. 6,362,005 B1 discloses a nitrogen dioxide gas sensing method based on the basic Saltzman method wherein a mixture of a diazotizing reagent which reacts with nitrous ions to produce a diazo compound and a coupling reagent that couples with a diazo compound to produce an azo dye are impregnated into a porous glass chip having fixed dimensions. An acid is also placed in the pores of this transparent body. The sensor element is placed in between a light emitting diode and a phototransistor followed by a voltmeter which measures the voltage difference. In this sensor, an easy leaching of the reagents from the pores of the sensor element is a serious problem. This limits the suitability of the sensor in different environmental conditions and also for long term use.

U.S. Pat. No. 5,567,622 describes a fiber optic chemical dosimeter system capable of detecting the presence of hydrazine fuels and nitrogen tetroxide and nitrogen dioxide gases that are used at rocket launch sites. The sensor is based on the detection of optical reflections from different sensor sites by the interrogation of infrared or visible red laser by an optical time domain reflectometry (OTDR) monitor.

There still exists a need for a durable and low cost device capable of detecting nitrogen oxide gases quantitatively and at low concentrations.

SUMMARY OF THE INVENTION

According to a first embodiment of the invention, a method of making a nitrogen oxide sensing element is provided which includes: incorporating a diazotizing reagent which reacts with nitrous ions to produce a diazo compound and a coupling reagent which couples with the diazo compound to produce an azo dye into a sol; and allowing the sol to form gel. According to this aspect of the invention, the gel comprises a microporous optically transparent inroganic matrix comprising immobilized diazotizing reagent and immobilized coupling reagent. A nitrogen dioxide sensing element made by a method as set forth above is also provided. The sensing element can be a cylindrical solid body or a film. Also provided is a nitrogen dioxide sensor comprising: a sensing element as set forth above; a light source; and an optical detector; wherein the sensing element is coupled to the light source by one or more transmitting optical fibers and wherein the sensing element is coupled to the detector by one or more receiving optical fibers such that light from the light source is transmitted through the one or more transmitting optical fibers and impinges on the sensing element and light impinging on the sensing element is transmitted through the one or more receiving optical fibers to the detector.

According to a second embodiment of the invention, a nitrogen oxide sensing element is provided which comprises: a microporous matrix of an optically transparent inorganic compound; a diazotizing reagent which reacts with nitrous ions to produce a diazo compound; and a coupling reagent which couples with the diazo compound to produce an azo dye; wherein the diazotizing reagent and the coupling reagent are immobilized in the microporous matrix.

According to a third embodiment of the invention, a nitrogen oxide sensor is provided which comprises: a film sensing element comprising a microporous matrix of an optically transparent material, a diazotizing reagent which reacts with nitrous ions to produce a diazo compound and a coupling reagent which couples with the diazo compound to produce an azo dye; a light source; and an optical detector. According to this aspect of the invention, the sensing element is coupled to the light source by one or more transmitting optical fibers and the sensing element is coupled to the detector by one or more receiving optical fibers such that light from the light source is transmitted through the one or more transmitting optical fibers and impinges on the sensing element and light impinging on the sensing element is transmitted through the one or more receiving optical fibers to the detector. Also according to this aspect of the invention, ends of the transmitting and receiving fibers adjacent the sensing element are positioned on the same side of the film sensing element.

DETAILED DESCRIPTION

The present invention relates to a nitrogen dioxide gas sensing method based on fiber optic absorption spectroscopy. Here the sensor system comprises an excitation light source, a sensor element, a multimode optical fiber and a miniaturized fiber optic spectrometer operating in the UV-VIS spectral range. The sensor element comprises specific reagents responsible for the $NO_2$ sensing immobilized in a porous structure by the sol-gel process. The sensing element can be made into a thin sol-gel disc or it can be cast in a tube (e.g., a fluoropolymer tube such as a polytetrafluoroethylene tube) to form a solid sol-gel core. Various embodiments of sensors are described herein which are suitable to the measurement of different $NO_2$ concentrations.

Figure 2A:
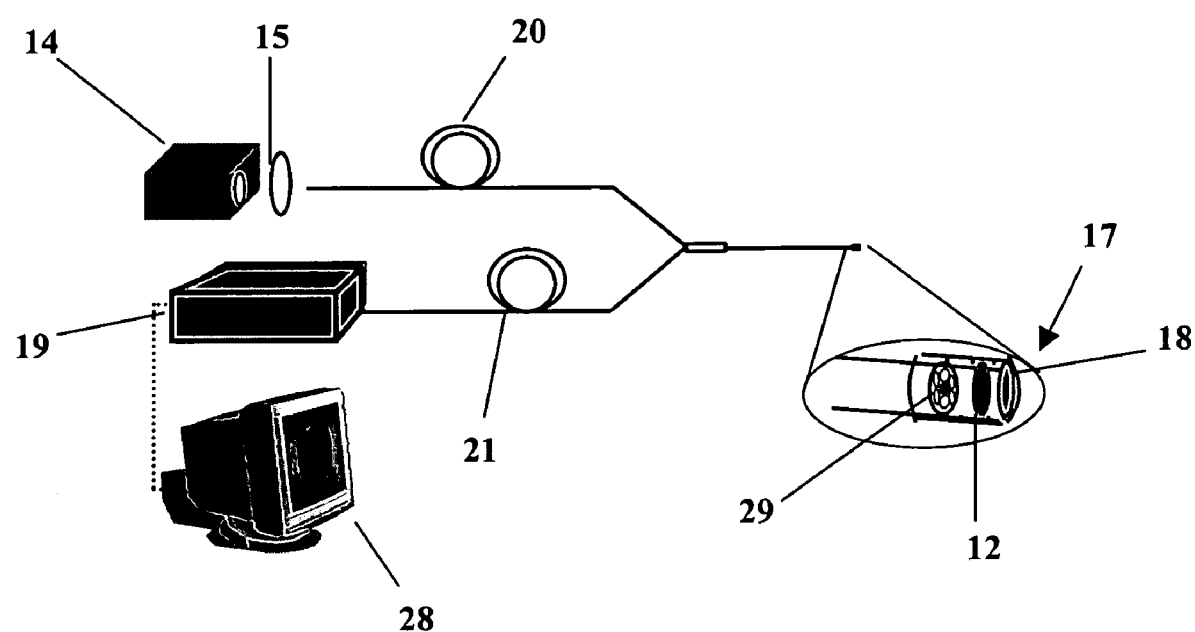
FIGS. 2A to 2D are schematics of various embodiments of sensors described in the present application which can be used to detect nitrogen dioxide in air samples.
Figure 2B:
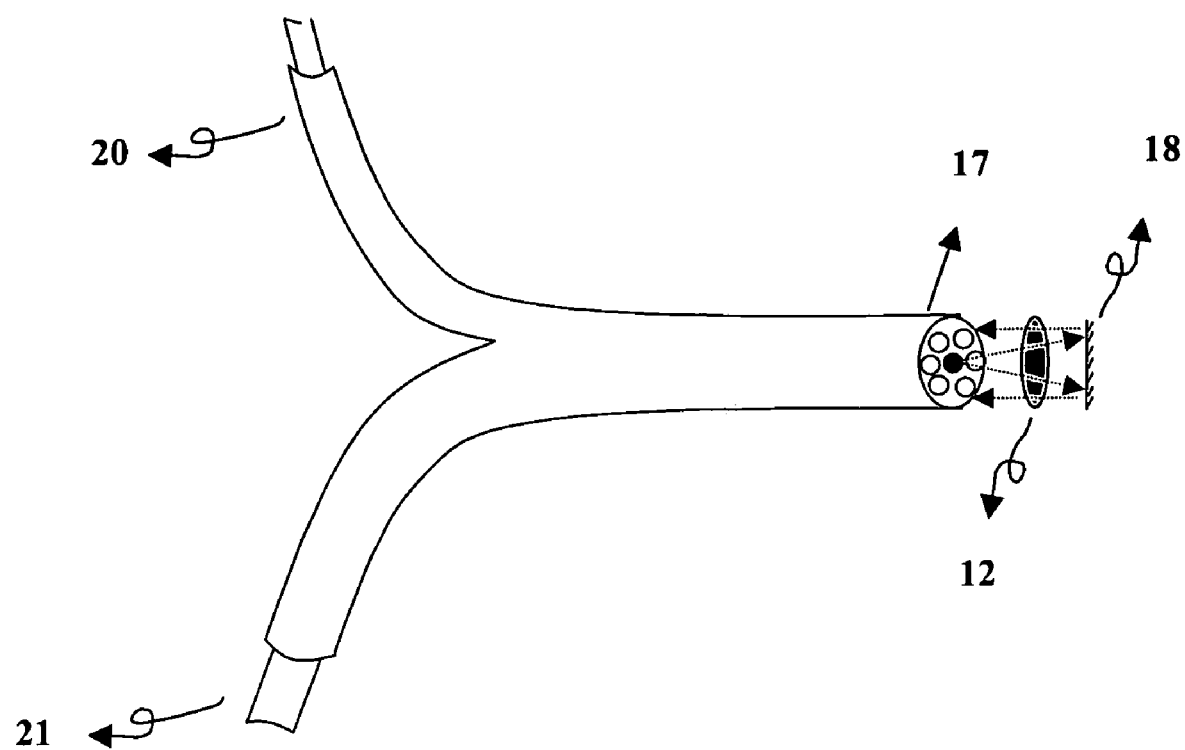

According to a first embodiment, the sensing element is disc shaped (i.e., a sol-gel disc). Multimode optical fibers comprising one or more illumination fibers and one or more read fibers can be connected to the disc sensor to form a transflection probe. A sensor according to this embodiment is shown in FIG. 2B. In use, light is transmitted through the illumination fiber (20) and through the sensing element (12) to impinge a flat mirror (18). The light is reflected off of the mirror (18) and travels through the sensing element (18) a second time and onto the ends of the read fibers (21). The reflected light is then transmitted through the read fibers (21).

Figure 2C:
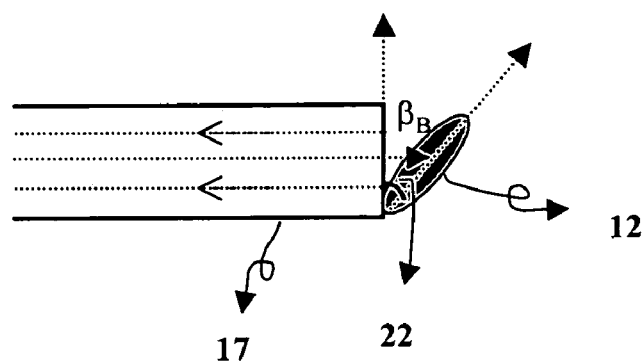

A sol-gel disc sensor can also be combined with multimode optical fibers to form a probe wherein the sensing element which is placed at an angle (e.g., a Brewster angle $\beta_B$) to the fiber bundle. A sensor according to this embodiment of the invention is shown in FIG. 2C. According to the embodiment shown in FIG. 2C, light travels through the illumination fiber (20) to the sensing element (12). The light is reflected from the sensing element (12) onto the read fibers (21).

Figure 2D:
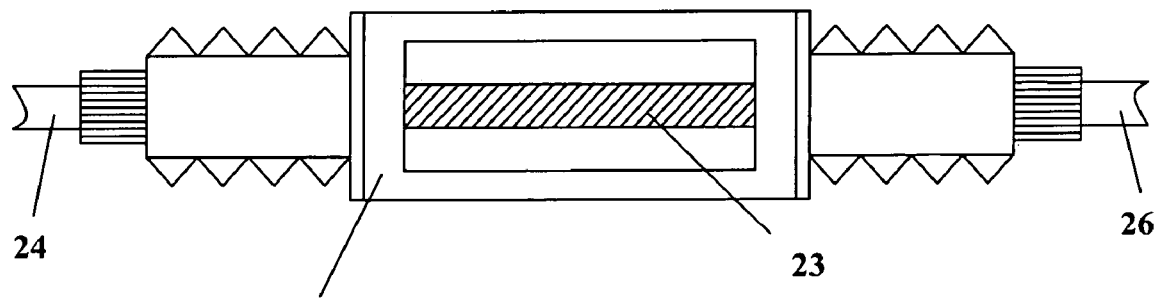

The sensing element can also be in the form of a solid sol-gel core. One embodiment of a sensor comprising a sol-gel core sensing element is shown in FIG. 2D wherein multimode optical fibers (24) are combined to form a probe. In use, light travels from the illumination fiber through a solid sol-gel core sensing element (23) and onto the read fibers (24). In this embodiment, the sensing element can be made of varying thickness and lengths depending on the level of sensitivity required.

One objective of the present invention is to develop a simple and accurate technique for the detection of nitrogen dioxide gas that offers high sensitivity and selectivity. The sensor comprise a sensing element has a porous structure with high interconnectivity that can be tailored into different design configurations.

Sensor Element Preparation

The $NO_2$ sensor element comprises a highly reactive sensing material encapsulated into the pores of a transparent porous body through the sol-gel process. The sol-gel process is explained in detail in Rabinovich, "Sol-gel Processing—General Principles", Sol-gel Optics Processing and Applications, C. K. Lisa, ed.; Kulwer Academic, Boston (1994). Normally the sol-gel is formed by the hydrolysis and polymerization of metal alkoxides or metalorganic compounds at lower temperature. The glass formed by this method is a porous matrix that contains interconnected pores formed by a three-dimensional network of $SiO_2$.

Reagents sensitive to nitrogen oxides can be incorporated into the sol-gel matrix to detect nitrogen oxides such as nitrogen dioxide at very low concentration. To prepare a sensing element, a diazotizing reagent and a coupling reagent can be mixed and the resulting reactant mixture can be added to the sol. According to one embodiment, the diazotizing reagent and the coupling reagent can be mixed in equal proportions. After gelation of the sol-gel matrix, the diazotizing and coupling reagents are immobilized in the sol-gel matrix.

As set forth above, the sensing element can be cast or otherwise formed into various configurations including a thin disc. Alternatively, the sol can be cast into the cavity of a mold (i.e., into a tube) to form a solid core sensing element.

When the sensor element is exposed to an atmosphere containing nitrogen dioxide gas, the diazotizing reagent diazotizes the nitrous ions produced by nitrogen dioxide adsorbed to the pores of the sensor element to produce a diazo compound. The coupling reagent couples with the diazo compound to produce an azo dye. A color change is observed from pink to red in the sensor element and consequently a variation in the optical absorption of the sensing film is observed at specific wavelengths. The temporal response of the absorption spectrum at various $NO_2$ concentrations has been recorded and analyzed.

Transflection Probe

A transflection fiber optic sensor according to one embodiment is shown in FIG. 2B. According to this embodiment, the sensor comprises a Y-shaped fiber bundle (17) comprising one central illumination fiber 20 surrounded by six receiving fibers (21). A sensing element (12) as a sol-gel film is placed at the distal end of this fiber bundle. In the embodiment shown in FIG. 2B, a mirror (18) placed behind the sensor film can be used to enhance the back reflection of the transmitted light through the film. The light transflected from the sensing film is detected and analyzed (e.g., using a fiber optic spectrometer).

Brewster Angle Probe

In this embodiment, which is shown in FIG. 2C, the probe can comprise a Y-shaped fiber bundle (17) with one central illumination fiber (20) surrounded by a plurality (e.g., six) receiving fibers (21) with the sensor element in the form of a sol-gel film (12) placed at a Brewster angle to the end of the fiber bundle. According to this embodiment, a mirror does not need to be used behind the sensor element. This configuration shows better performance at lower concentration in the range of few parts per million of $NO_2$ in air. At the Brewster angle, the transflected light from the sensing film is transmitted through the receiving fibers. This light can be detected and analyzed (e.g., using a fiber optic spectrometer).

Probe with Solid Core Sensor

In this embodiment, the sensing element, as a solid sol-gel core (23), is placed in between two multi-mode fibers (24) in a fiber holder (25). The fiber holder can include a spring arm adapted to grab the fibers (24) upon insertion. The fiber holder can also have a locking nut as well as a collet to hold the fibers (24) in position.

In use, the illuminating fiber at one end of the sensing element transmits light through the sensing element and the light is collected by the second fiber which is placed at the other end of the sensing element and fed to the analyzer (e.g., a fiber optic spectrometer). This design has been used to detect $NO_2$ at low concentrations.

Three different embodiments of fiber optic sensors are described above. FIG. 2A represents the schematic of an experimental set-up developed for the characterization of sensors at different nitrogen dioxide concentrations. As shown in FIG. 2A, a fiber probe 17 comprising a sensing element 12 (shown in the form of a sensing film) is in optical communication with a light source 14 and a detector 19. In particular, a first optical fiber 20 can transmit light from the light source to the sensing element 12 and a second optical fiber 21 can transmit light from the sensing element to the detector 19. A computer 28 is shown interfaced with the detector 19. In use, light from light source 14 passes through lens 15 and is transmitted down optical fiber 20 through fiber bundle end 29 to sensing element 12. Light impinging on sensing element 12 passes through sensing element 12 and is reflected by mirror 18, through sensing element 12 and into ends of optical fiber 21. Light is then transmitted through optical fiber 21 to detector 19. Data from detector is then collected on computer 28. According to one embodiment, the light source can emit white light.

Preparation of an $NO_2$ Sensor Element

Preparation procedures for a nitrogen dioxide gas-sensing element are described below. The sensing element is an optically transparent porous material encapsulated with the highly sensitive reagents (8, 10) which produce a specific coloration reaction in the micropores of the material. The immobilization of these highly sensitive reagents in the porous structure can be achieved through a sol-gel process.

A typical reaction scheme which takes place in a sol-gel process is set forth below.

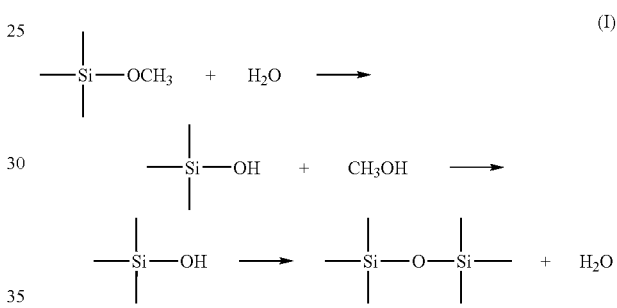

As shown above, the precursor for the reaction in the sol-gel process can be tetra methyl orthosilicate (TMOS). As also shown above, the TMOS is mixed with water (e.g., deionized water). The TMOS is preferably mixed with water at a specific molar ratio of 2:1. The mixture can then be sonicated for five minutes in a sonicator to initiate the polymerization reaction. A few minutes after the sonication, an acid (e.g., 60 mL of 0.04 molar HCl) can be added to the reaction mixture followed by a gentle mixing with a magnetic stirrer for a few minutes which catalyzes the polymerization reaction further.

As shown above, hydrolysis can then occur which results in the formation of silanol groups (i.e., Si—OH). The silanol groups can then react further to from siloxane polymers (i.e., Si—O—Si) in the condensation reaction.

To make a sensing element, a diazotizing reagent and a coupling reagent can be combined with the sol. According to one embodiment, sulfanilamide (SFA) is used as a diazotizing reagent and N,N-dimethyl-1-naphthylamine (DMNA) is used as a coupling reagent. The structures of these two compounds are shown below.

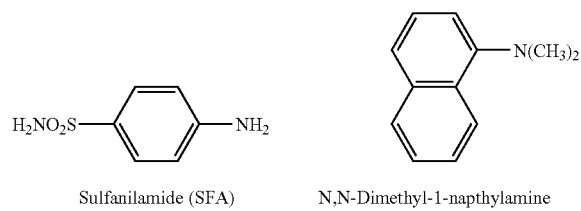

Sulfanilamide (SFA)    N,N-Dimethyl-1-napthylamine

According to one embodiment, equal quantities of a 0.25 molar solution of sulfanilamide (SFA) prepared in 5N acetic acid can be thoroughly mixed in 0.25 molar solution of N,N-dimethyl-1-naphthylamine (DMNA) prepared in 5N acetic acid. This mixture solution can then be kept in an amber colored container. One ml of the above solution can then be added to the sol as set forth above before it starts the polymerization and condensation process. The sol can then again be mixed thoroughly to produce a homogenous distribution of the reagents in sol-gel.

After a few hours, the sol can be formed into the sensing element. For example, the sol can be formed into a thin sol-gel disc to make a film sensing element (12) or poured into a tube to make a solid core sensor element (23). After formation, the sensing element can be kept for one week at room temperature to complete the gelation process.

Figure 1:
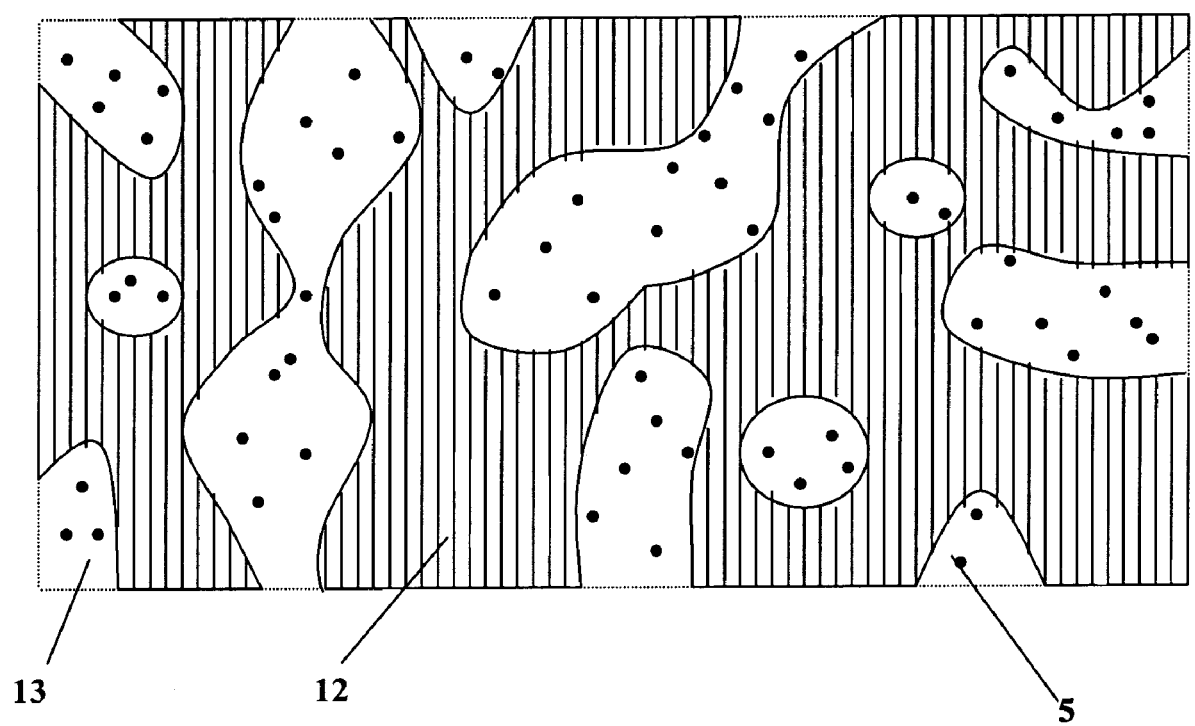
FIG. 1 is a schematic of a sensing element according to one embodiment of the invention showing $NO_2$ gas entering the pores of a microporous inorganic matrix.

An $NO_2$ sensing element according to one embodiment is shown in FIG. 1. As shown in FIG. 1, the $NO_2$ sensing element comprising an inorganic matrix 12 having pores 13 (e.g., micropores) and comprising an $NO_2$ sensing reagent and a coupling reagent immobilized in the micropores 13. The sensing element can exhibit a color change in the presence of nitrogen dioxide gas. For example, when nitrogen dioxide gas 5 enters pores 13 of the sensor element, it can be adsorbed onto the surfaces of the pores. According to the reaction set forth below, nitrous $NO_2^-$ and nitric ions $NO_3^-$ can be produced at the sol-gel pores.

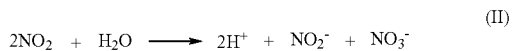

$$2NO_2 + H_2O \longrightarrow 2H^+ + NO_2^- + NO_3^- \qquad (II)$$

The diazotizing reagent (e.g., SFA) immobilized in the pores can then react with nitrous ions produced by the nitrogen dioxide gas to make a diazo compound (e.g., an SFA diazonium salt) as set forth below.

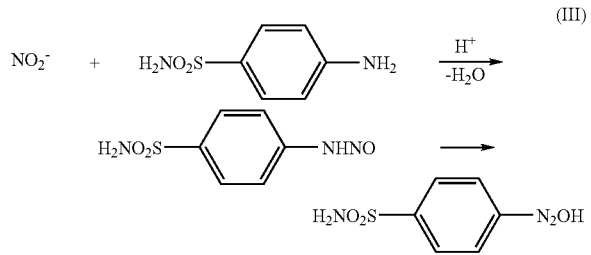

(III)

The coupling reagent can then couple with this diazo compound to produce an azo dye as shown below.

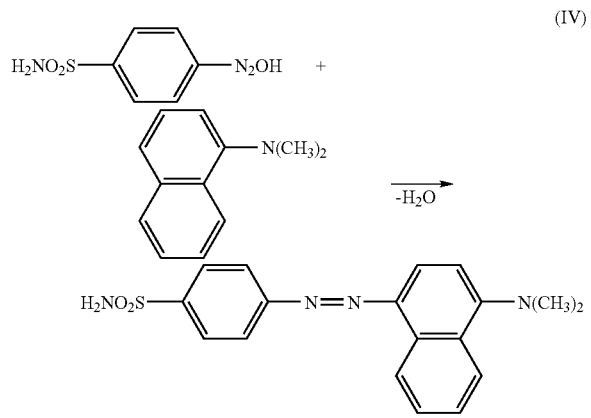

(IV)

Consequently, a color change in the sensing element can be produced.

The $NO_2$ sensor element prepared through the above-described procedure has specific advantages over other conventional polymer supports. For example, sol-gel supports are typically more resistant to aggressive environments than conventional polymer supports, since polymer matrices suffer degradation when they are exposed to environments that contain organic vapors or, even, to slightly elevated temperatures. Also most of the organic polymer matrices are photochemically and thermally unstable.

Transflection Probe

In one embodiment, the $NO_2$ sensor element is prepared as a thin sol-gel disc or film having a diameter about 4 mm and with thickness of about 1 mm. The sensor can comprise a fiber optic transflection probe as shown in FIG. 2B. The probe consists of a Y-shaped fiber bundle 17, which has a central illumination fiber 20 having core diameter of 200 mm surrounded by six signal receiving fibers 21 with the same dimension, the $NO_2$ sensor element film 12, and a reflecting mirror 18. The $NO_2$ sensor element film is placed at a right angle to the fiber bundle at the distal end of this fiber bundle with the reflecting mirror placed just behind the sensor element. The $NO_2$ sensor element is excited with a white light source 14 (ORIEL 66001). The reflecting mirror 18 redirects the transmitted light signal back through the sensor element to the receiving fiber bundle 21.

Figure 3:
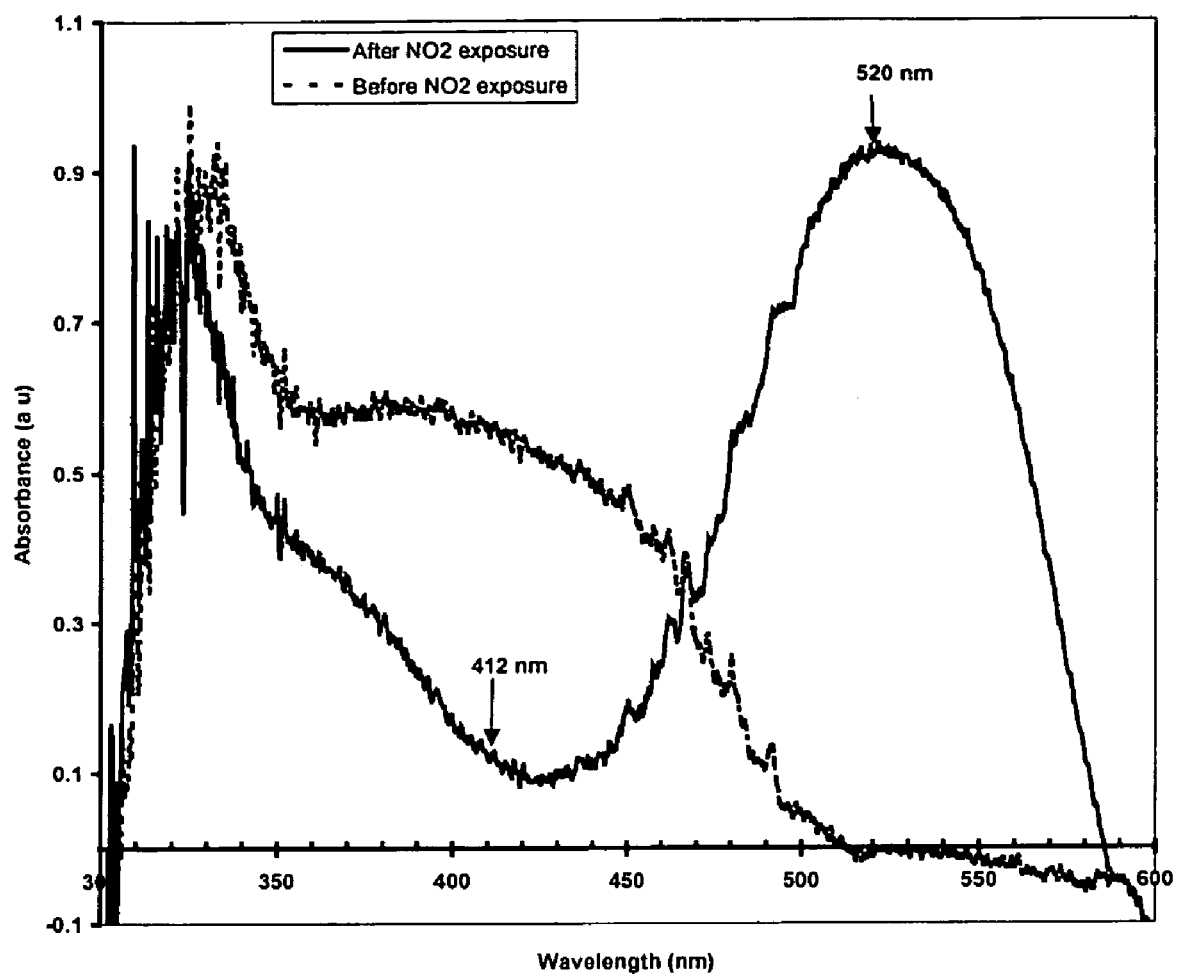
FIG. 3 is an absorption spectrum of a sensing element as set forth in FIG. 2B before and after $NO_2$ exposure.

The temporal response of the absorption spectrum of the sensor element at various $NO_2$ concentrations is recorded and analyzed in the current fiber optic sensor configuration. This can be accomplished with a fiber optic spectrometer 19 (USB 2000, Ocean Optics), which consists of a Grating placed in front of a CCD. The data can be acquired by use of a DAQ card and connected to a personal computer. The spectral variation is then recorded with OOIBase software purchased from Ocean Optics. FIG. 3 represents the spectral response of the fiber optic sensor before and after the $NO_2$ exposure.

Figure 4:
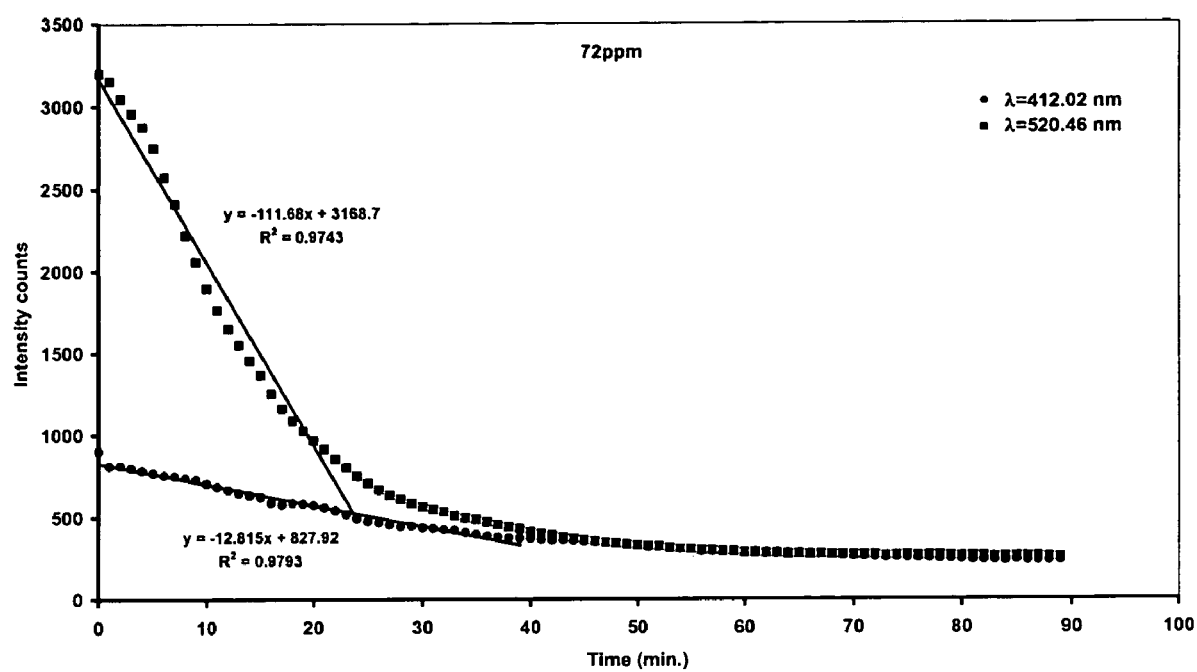
FIG. 4 is a plot showing a typical temporal response at two different absorption peak wavelengths (i.e., 412.02 nm and 520.46 nm) and at a $NO_2$ concentration of 72 ppm of a fiber optic sensing element as set forth in FIG. 2B.

As can be seen from FIG. 3, two prominent absorption peaks at about 520 nm and about 412 nm respectively, can be observed which represent the characteristic response of the sensor element at a typical $NO_2$ concentration in air. FIG. 4 gives the intensity variation of the sensor with a fixed interval of time on exposure to a 72 ppm $NO_2$ in air at 520 nm and 412 nm respectively. Spectral response with a LED emitting at 520 nm is recorded with the same sensor configuration.

Figure 5:
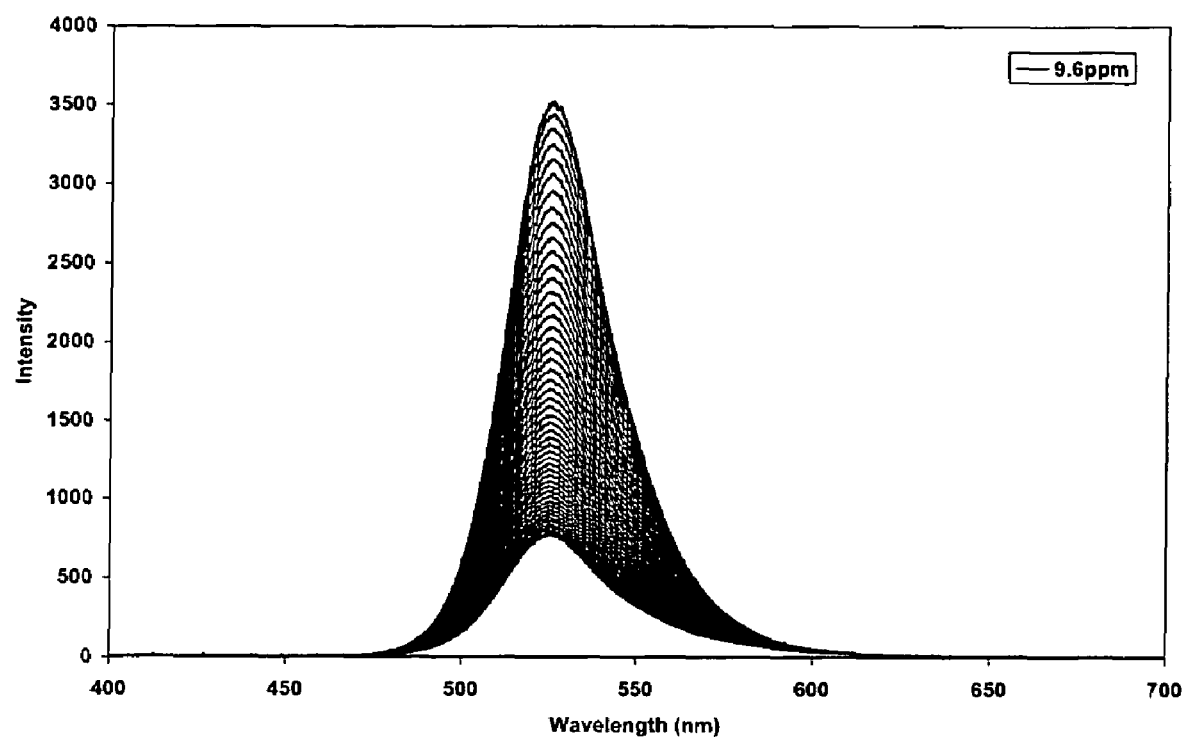
FIG. 5 is a plot showing the spectral response of a sensor as set forth in FIG. 2B at an $NO_2$ concentration of 9.6 ppm.

FIG. 5 is a plot showing the spectral response at 9.6 ppm $NO_2$ using an LED as a light source.

Brewster Angle Probe

According to a further embodiment, a film sensing element can be placed at an angle (i.e., Brewster's angle) to the end of a fiber bundle comprising transmitting and receiving fibers such that a mirror is not required. This embodiment is shown in FIG. 2C. The probe can comprise a Y-shaped fiber bundle (17) which has a central illumination fiber (20) (e.g., having a core diameter of 200 mm) surrounded by a plurality (e.g., six) signal receiving fibers (21). The fibers can all have the same dimensions. A sensing element having, for example, a diameter of about 4 mm and a thickness of about 1 mm can be placed at Brewster's angle to the fiber bundle.

FIG. 2C provides the schematic representation of a fiber optic sensor according to this embodiment. For glass and other dielectric materials, at Brewster angle ($\beta_B$) 22, electromagnetic waves with a plane of vibration perpendicular to the plane of incidence are completely reflected back from the sensor element. As a result, this configuration does not require any additional mirror behind the sensor element. In this configuration, the transflected light from the sensing film is also partially polarized.

Figure 6:
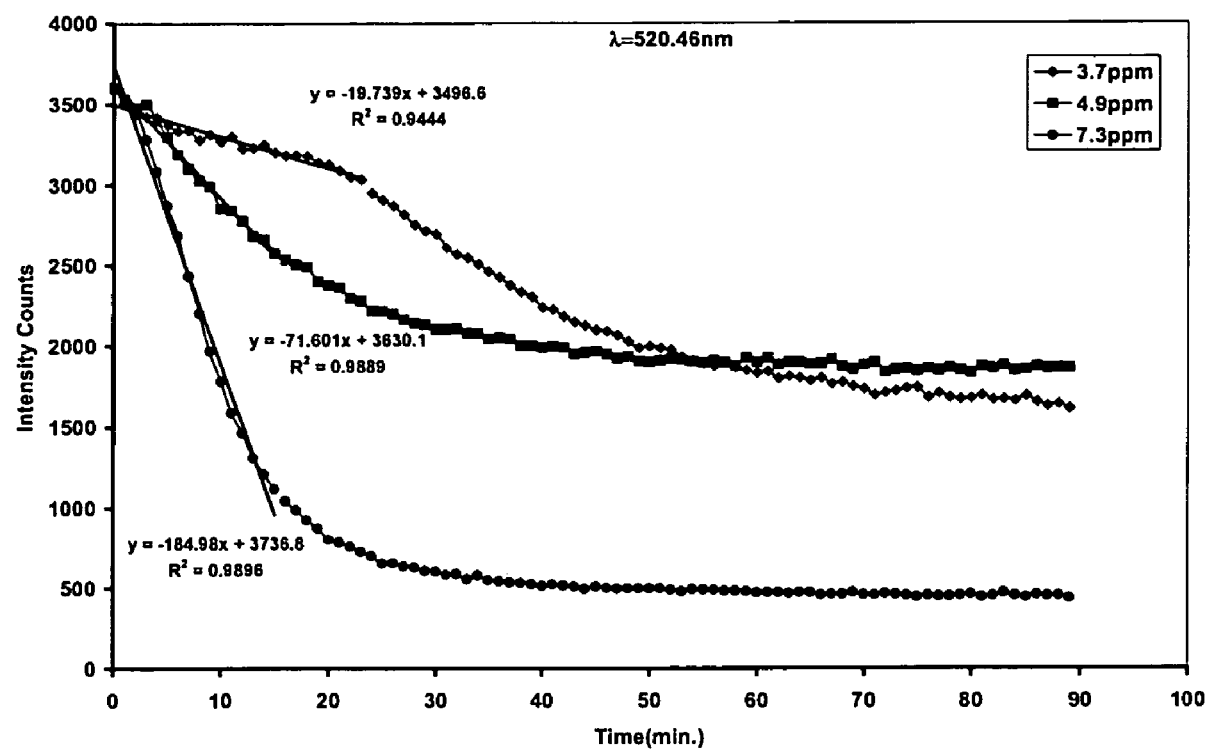
FIG. 6 is a plot showing the temporal response of the fiber optic sensor as set forth in FIG. 2C at three different nitrogen dioxide concentrations (i.e., 3.7, 4.9, and 7.3 ppm).

This embodiment shows better performance at lower nitrogen dioxide concentration (e.g., in the range of few parts per million of $NO_2$ in air). FIG. 6 represents fiber optic sensor responses at 3.7 ppm, 4.9 ppm and 7.3 ppm of $NO_2$ concentrations in air for a sensor according to this embodiment of the invention. The plot reveals the intensity variation at 520 nm with respect to time at three different $NO_2$ concentrations. The temporal response depicts the capability of the present fiber optic sensor design for the quantitative detection of nitrogen dioxide gas.

Figure 7:
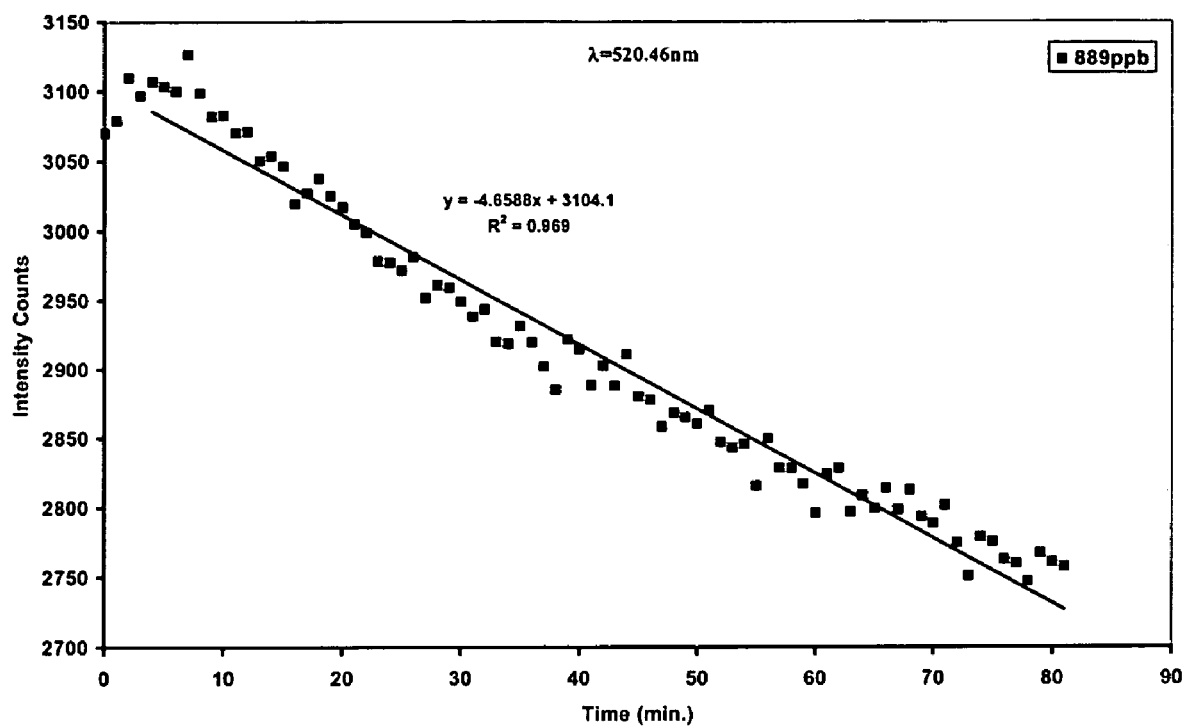
FIG. 7 is a plot showing the time vs intensity plot of a fiber optic sensor as set forth in FIG. 2C at a typical $NO_2$ concentration of 889 ppb.

FIG. 7 shows the intensity vs. time plot of the a fiber optic sensor according to this embodiment of the invention wherein the sensing element is placed at the Brewster's angle to the direction of incidence. This embodiment provides the temporal response of the sensor at a peak absorption wavelength at 520 nm with $NO_2$ concentration of 889 ppb in air.

Solid Sol-Gel Core Probe

According to a further embodiment, a sensing element having a solid core configuration can be used. According to this embodiment, the sensing element, which acts as the transducer, comprises an immobilized diazotizing reagent as well as a coupling reagent mixed. The diazotizing and coupling reagents can be present in equal molar proportions.

A sensor according to this embodiment of the invention is shown in FIG. 2D. As shown in FIG. 2D, the sensing element core can be placed in between two multimode fibers 24, 26 (e.g., fibers having a core diameter of 600 mm). The fiber ends can be placed in a fiber holder 25 which has a spring arm that grabs the fiber upon insertion. This fiber holder 25 has a locking nut as well as a collet to hold the fibers 24 in position. The illuminating fiber at one end of the sol-gel core 24 transmits light into and through the sensing element core 23. This light is recollected by the second or receiving fiber 26 which is placed at the other end of the sensing element. The light collected by the receiving fiber 26 can then be fed to a detector (e.g., a fiber optic spectrometer).

The solid core sensing element 23 prepared as above can be used for detecting nitrogen oxide gas (e.g., nitrogen dioxide gas) in the environment. The $NO_2$ sensing reagents immobilized in the micropores 13 of the sensor element results in the coloration reaction in the presence of nitrogen dioxide gas. When the nitrogen gas 5 enters the micropores 13 of the sensor element, it is adsorbed to the pores. According to the reaction set forth above in reaction scheme (II), nitrous ions and nitric ions can then be produced at the sol-gel pores. The diazotizing reagent can then react with the nitrous ions produced by the nitrogen dioxide gas to make a diazo compound as set forth in reaction scheme (III), above. The coupling reagent can then couple with this diazo compound to produce an azo dye as shown in reaction scheme (IV), above. This reaction can result in a color change in the sensing element.

The color change can be recorded with a detector such as a fiber optic spectrometer (e.g., USB 2000, Ocean Optics). The spectrometer can, for example, comprise a grating placed in front of a CCD. The data can be acquired, for example, by use of a DAQ card and connected to a personal computer. The spectral variation can then be recorded (e.g., with OOIBase software purchased from Ocean Optics).

Figure 8:
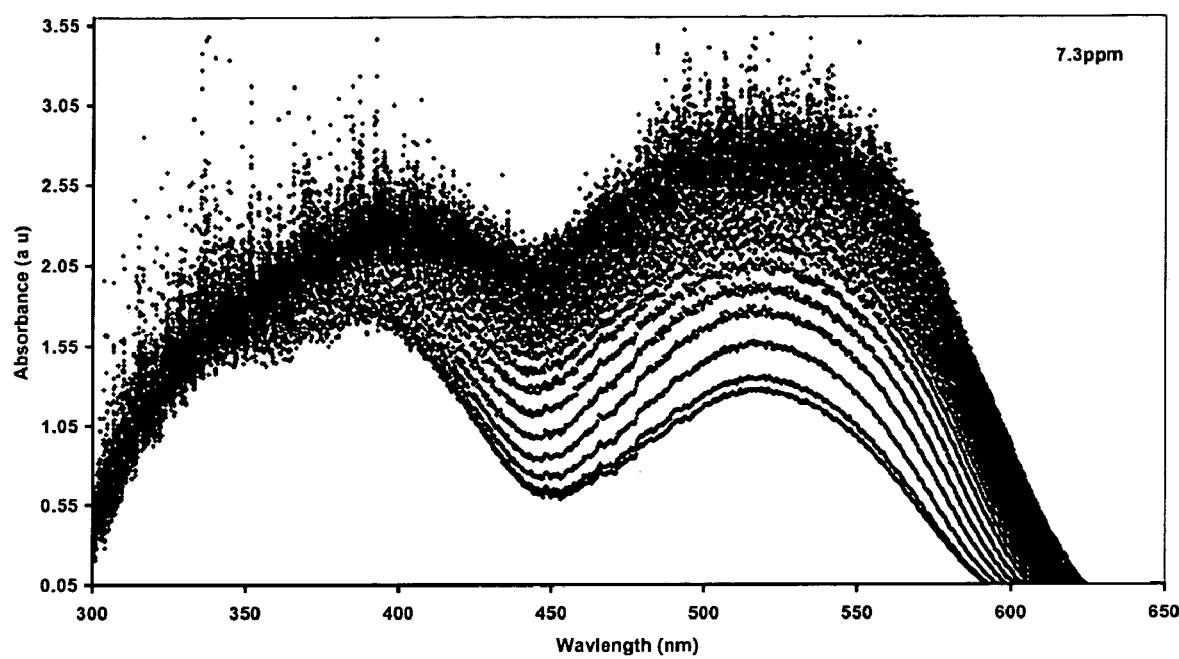
FIG. 8 is a plot showing the spectral response of an $NO_2$ sensor with a solid sol-gel core as set forth in FIG. 2D.

FIG. 8 represents the typical absorption spectrum with the sol-gel fiber core as the sensor element at a nitrogen dioxide concentration of 7.3 ppm. Accordingly, when placed in an atmosphere to be measured, this present nitrogen dioxide gas sensor can sense nitrogen dioxide gas more simply and accurately than in conventional methods.

Figure 9:
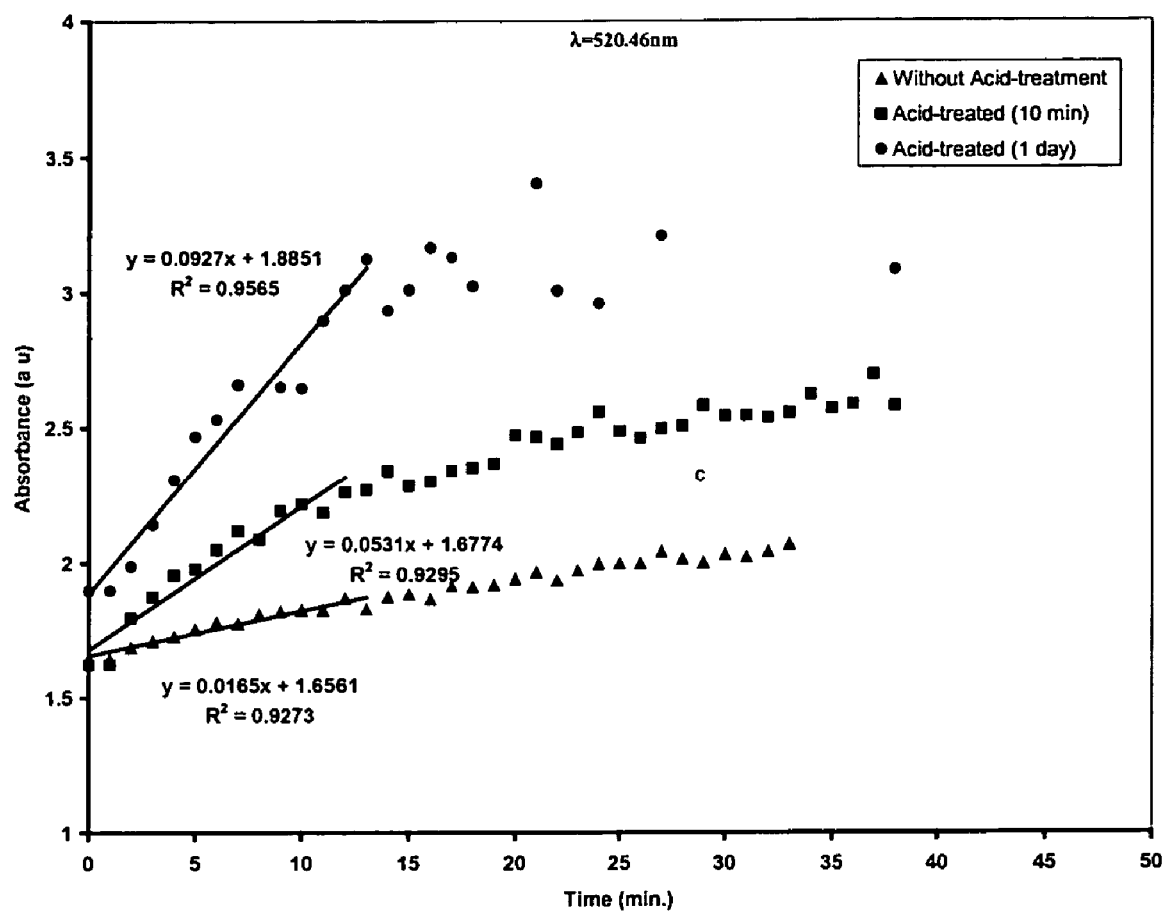
FIG. 9 is a plot showing the variation in the sensitivity of a fiber optic sensing element with a solid sol-gel core as set forth in FIG. 2D when the sensing element has been treated with mild acid for different time durations.

The coloration reaction at the sensor element according to this embodiment can be negligibly low due to the absence of acid in the pores of the sol-gel sensing element. In order to reactivate the sensing element, the sensing element can be treated with an acid (e.g., a mild acid) at different time durations. FIG. 9 shows the response of a solid core sensor wherein the sol-gel sensing element of the sensor has been treated with an acid for periods of 10 minutes and 24 hours. As can be seen from FIG. 9, the acid treated fiber optic sensor shows better sensitivity than the sensor with an untreated sensing element.

This embodiment of the $NO_2$ sensor is capable of detecting $NO_2$ at concentration levels as low as parts per billion in air samples. The utilization of a solid sol-gel core sensing element is an ideal way to make a highly sensitive optical fiber sensor. In this design, light from a light source is transmitted through the fiber and interacts with the sensing reagents distributed in the solid core sensing element to provide a very responsive sensor.

As set forth above, the sensing element can be in the form of a film (e.g., a thin film) or a solid body (e.g., an elongate solid body such as an elongate cylindrical solid). The film sensing element according to the invention can be a planar or substantially planar two-dimensional or sheet type structure. The film can be in the form of a circular disc.

According to one embodiment of the invention, the sensing element comprises a porous inorganic matrix into which the diazotizing reagent and the coupling reagent are immobilized. The term "immobilized" refers to the diazotizing reagent and the coupling reagent being integral to the microporous matrix (e.g., incorporated into the matrix during formation). By incorporating these reagents into the matrix itself, a sensing element having greater durability can be formed.

A compound which is an aromatic compound such as benzene, naphthalene, or biphenyl, or a heterocyclic aromatic compound such as thiophene or thiazole, and which has a primary amino group or an acetamide group can be used as the diazotizing agent. Exemplary diazotizing reagents include, but are not limited to, sulfanilamide (SFA), sulfanilic acid and acetanilide (AA).

A compound which is an aromatic compound such as benzene, naphthalene, or biphenyl, or a heterocyclic aromatic compound such as thiophene or thiazole, and which has an amino group (primary to tertiary), an alkoxy group, or a hydroxyl group can be used as the coupling reagent. Exemplary coupling reagents include, but are not limited to, N,N-dimethylnapthylamine (DMNA).

While the foregoing specification teaches the principles of the present invention, with examples provided for the purpose of illustration, it will be appreciated by one skilled in the art from reading this disclosure that various changes in form and detail can be made without departing from the true scope of the invention.

What is claimed is:

1. A nitrogen oxide sensor comprising:
  a nitrogen oxide sensing element made by a method comprising:
    incorporating a diazotizing reagent which reacts with
      nitrous ions to produce a diazo compound and a coupling reagent which couples with the diazo compound to produce an azo dye into a sol; and
allowing the sol to gel;
wherein the gel comprises a microporous optically transparent inorganic matrix comprising immobilized diazotizing reagent and immobilized coupling reagent;
a light source; and
an optical detector;
wherein the sensing element is coupled to the light source by one or more transmitting optical fibers and wherein the sensing element is coupled to the detector by one or more receiving optical fibers such that light from the light source is transmitted through the one or more transmitting optical fibers and impinges on the sensing element and light impinging on the sensing element is transmitted through the one or more receiving optical fibers to the detector;
wherein the sensing element is in the form of a film;
wherein ends of the transmitting and receiving fibers adjacent the sensing element are bundled into an optical fiber cable having a planar cable end adjacent the sensing element, and wherein the planar surface of the film sensing element is oriented at an angle to the planar cable end adjacent the sensing element; and
wherein the angle of orientation of the film sensing element to the planar cable end is the Brewster's angle ($\beta_B$) as calculated from the refractive index of the sensing element ($n_2$) and the refractive index of the medium through which the light travels before impinging on the sensing element ($n_1$) as set forth below:

$$\beta_B = \arctan\left(\frac{n_2}{n_1}\right).$$

2. The sensor of claim 1, wherein the sol comprises a metal alkoxide or a metalorganic compound.

3. The sensor of claim 1, wherein the sol comprises an alkoxy silane.

4. The sensor of claim 1, wherein the sol comprises tetramethyl orthosilicate (TMOS).

5. The sensor of claim 1, wherein the diazotizing reagent is sulfanilamide (SFA).

6. The sensor of claim 1, wherein the coupling reagent is N,N-dimethyl-1-naphthylamine (DMNA).

7. The sensor of claim 1, wherein the method for making the nitrogen oxide sensing element further comprises transferring the sol into the cavity of a mold and allowing the sol to gel in the mold.

8. The sensor of claim 7, wherein the mold is a tube and wherein the cavity of the mold is the hollow interior of the tube.

9. The sensor of claim 1, wherein the sol is formed into a film.

10. The sensor of claim 1, wherein the sensing element comprises equal molar proportions of diazotizing reagent and coupling reagent.

11. The sensor of claim 7, wherein the tube comprises polytetrafluorethylene (PTFE).

12. The sensor of claim 1, wherein the transmitting and receiving optical fibers are combined in the form of a Y-shaped optical cable having a single distal end comprising ends of both transmitting and receiving fibers, a first proximal end comprising the ends of one or more transmitting fibers and a second proximal end comprising the ends of one or more receiving fibers;
wherein the distal end of the Y-shaped optical cable is placed in optical communication with the sensing element;
wherein the first proximal end of the Y-shaped optical cable is placed in optical communication with the light source; and
wherein the second proximal end of the Y-shaped optical cable is placed in optical communication with the detector.

13. The sensor of claim 12, wherein the optical cable comprises a single transmitting fiber and a plurality of receiving fibers.

14. The sensor of claim 13, wherein the single transmitting fiber is surrounded by the plurality of receiving fibers at the distal end of the optical fiber cable.

15. The sensor of claim 13, wherein the optical cable comprises six receiving fibers.

16. The sensor of claim 1, wherein the light source has a spectral distribution ranging from 250 nm to 870 nm.

17. The sensor of claim 1, wherein the detector is a spectrometer.

18. The sensor of claim 17, wherein the spectrometer comprises a grating and a CCD, wherein light transmitted from the sensing element to the detector passes through the grating and impinges on the CCD.

19. The sensor of claim 1, further comprising a personal computer interfaced to the detector for collecting data.

20. A nitrogen oxide sensor comprising:
a film sensing element comprising a microporous matrix of an optically transparent material, a diazotizing reagent which reacts with nitrous ions to produce a diazo compound and a coupling reagent which couples with the diazo compound to produce an azo dye;
a light source; and
an optical detector;
wherein the sensing element is coupled to the light source by one or more transmitting optical fibers and wherein the sensing element is coupled to the detector by one or more receiving optical fibers such that light from the light source is transmitted through the one or more transmitting optical fibers and impinges on the sensing element and light impinging on the sensing element is transmitted through the one or more receiving optical fibers to the detector;
wherein ends of the transmitting and receiving fibers adjacent the sensing element are positioned on the same side of the film sensing element;
wherein the film sensing element is positioned such that light impinging on the sensing element is reflected by the sensing element into one or more receiving fiber ends;
wherein ends of the transmitting and receiving fibers adjacent the sensing element are bundled into an optical fiber cable having a planar cable end adjacent the film sensing element, and wherein the planar surface of the film sensing element is oriented at an angle to the planar cable end adjacent the sensing element; and
wherein the angle of orientation of the film sensing element to the planar cable end is the Brewster's angle ($\beta_B$) as calculated from the refractive index of the sensing element ($n_2$) and the refractive index of a medium through which the light travels before impinging on the sensing element ($n_1$) as set forth below:

$$\beta_B = \arctan\left(\frac{n_2}{n_1}\right).$$

21. The sensor of claim 20, wherein the sensor does not comprise a mirror.

* * * * *